US010265008B2

(12) United States Patent
Durkee et al.

(10) Patent No.: US 10,265,008 B2
(45) Date of Patent: Apr. 23, 2019

(54) SYSTEMS AND METHODS TO DETERMINE USER STATE

(71) Applicant: Aptima, Inc., Woburn, MA (US)

(72) Inventors: Kevin Durkee, Beavercreek, OH (US); Scott Pappada, Fairborn, OH (US); Andres Ortiz, Simi Valley, CA (US); William DePriest, Dayton, OH (US); John Feeney, Beavercrek, OH (US); Alexandra Geyer, Winchester, MA (US); Seamus Sullivan, Oakwood, OH (US); Sterling Wiggins, Yellow Springs, OH (US)

(73) Assignee: Aptima, Inc., Woburn, MA (US)

( * ) Notice: Subject to any disclaimer, the term of this patent is extended or adjusted under 35 U.S.C. 154(b) by 600 days.

(21) Appl. No.: 14/772,827

(22) PCT Filed: Mar. 13, 2014

(86) PCT No.: PCT/US2014/025152
§ 371 (c)(1),
(2) Date: Sep. 4, 2015

(87) PCT Pub. No.: WO2014/159793
PCT Pub. Date: Oct. 2, 2014

(65) Prior Publication Data
US 2016/0007899 A1    Jan. 14, 2016

Related U.S. Application Data

(60) Provisional application No. 61/779,862, filed on Mar. 13, 2013.

(51) Int. Cl.
*A61B 5/0476*    (2006.01)
*G09B 23/28*    (2006.01)
(Continued)

(52) U.S. Cl.
CPC .......... *A61B 5/165* (2013.01); *A61B 5/04012* (2013.01); *A61B 5/0476* (2013.01);
(Continued)

(58) Field of Classification Search
CPC ... A61B 5/165; A61B 5/04012; A61B 5/0476; A61B 5/7203; A61B 5/7246;
(Continued)

(56) References Cited

U.S. PATENT DOCUMENTS

2003/0013981 A1    1/2003    Gevins et al.
2011/0105855 A1    5/2011    Johnson
(Continued)

OTHER PUBLICATIONS

Durkee, K., Geyer, A., Pappada, S., Oritz, A., Galster, S., Real-Time Workload Assessment as a Foundation for Human Performance Augmentation in Lecture Notes in Computer Science, 8027; 279-288; Foundations of augmented cognition: 7th International Conference, AC 2013, held as part of HCI International 2013, Las Vegas, NV, USA, Jul. 21-26, 2013, proceedings /by Springer, Heidelberg; 2013.
(Continued)

*Primary Examiner* — Navin Natnithithadha
(74) *Attorney, Agent, or Firm* — John J. Brooks, III

(57) ABSTRACT

Computer based systems and methods for estimating a user state are disclosed. In some embodiments, the methods comprise inputting a first input at an intermittent interval and a second input at a frequent interval into a user state estimation model to estimate the user state. In some embodiments, the first inputs are enhanced by injecting a noise input to create a plurality of enhanced first inputs whereby the plurality of enhance first inputs correspond to the plurality of second inputs at the frequent interval. In some embodiments, the first input comprises a self-reported input and the second inputs comprise a physiological input, a performance input or a situational input. In some embodiments, a machine
(Continued)

learning algorithm creates the state estimation model. In some embodiments, the state estimation model estimates a future user state. In some embodiments, a computer based system for estimating a user state is provided.

20 Claims, 10 Drawing Sheets

(51) Int. Cl.
G16H 50/30 (2018.01)
A61B 5/16 (2006.01)
A61B 5/04 (2006.01)
A61B 5/00 (2006.01)

(52) U.S. Cl.
CPC .......... *A61B 5/7203* (2013.01); *A61B 5/7246* (2013.01); *A61B 5/7267* (2013.01); *A61B 5/7475* (2013.01); *G09B 23/28* (2013.01); *G16H 50/30* (2018.01)

(58) Field of Classification Search
CPC .... A61B 5/7267; A61B 5/7475; G09B 23/28; G06F 19/3431
USPC ................................................ 600/544, 545
See application file for complete search history.

(56) References Cited

U.S. PATENT DOCUMENTS

2012/0123232 A1    5/2012  Najarian et al.
2012/0245439 A1*   9/2012  Andre .................. A61B 5/0205
                                                        600/310
2014/0221850 A1*   8/2014  Farringdon .......... A61B 5/0428
                                                        600/483

OTHER PUBLICATIONS

Lee W. Young, International Search Report and Written Opinion for parent application PCT/US14/25152, dated Aug. 11, 2014, 10 pgs, USPTO, Alexandria, VA, USA.

Wang, Z., et al., Cross-subject workload classification with a hierarchical Bayes model, NeuroImage (2011), vol. 59, Issue 1, Jan. 2, 2012, pp. 64-69, Available online Aug. 16, 2011, 6 pgs.

* cited by examiner

US 10,265,008 B2

SYSTEMS AND METHODS TO DETERMINE USER STATE

CROSS-REFERENCE TO RELATED APPLICATIONS

This invention claims benefit of U.S. Pat. App. No. 61/779,862, entitled "SYSTEMS AND METHODS TO DETERMINE USER STATE", filed Mar. 13, 2013, the entire contents of which are herein incorporated by reference.

STATEMENT REGARDING FEDERALLY SPONSORED RESEARCH OR DEVELOPMENT

This invention was made with Government support under Contract No. FA8650-11-C-6236 awarded by the U.S. Air Force. The Government has certain rights in the invention.

REFERENCE TO SEQUENCE LISTING, A TABLE, OR A COMPUTER PROGRAM LISTING COMPACT DISC APPENDIX

Not Applicable.

BACKGROUND OF THE INVENTION

1. Field of the Invention

The disclosed systems and methods relate to automatically determining a state of a system user. Particularly, in one claimed embodiment, the methods relate to determining a state of the user based on modeling the user state with physiological and self-reported measures.

2. Background

The ability to develop algorithms that estimate human user states in real-time settings based on physiological inputs has been limited. Almost exclusively, scientists have relied on machine learning techniques to train these algorithms to find optimal weights among a data set that best match a particular measure of human user state. However, standard machine learning practices have produced user state estimation algorithms that suffer from low resolution (e.g., low vs high workload), infrequent updates (e.g., once per minute), and poor generalizability across human operators. There is no standard defined process that sufficiently overcomes these limitations through a single approach. Variations of machine learning practices, such as artificial neural networks (ANN) and support vector machines (SVM), have been used across scientific communities in an attempt to create user state estimation algorithms. Some scientists have attempted to produce high output resolution for user state estimation algorithms by creating a laboratory based task environment that varies a human operator's functional state (e.g., workload) across many levels, collecting self-reported metrics for the state of interest within each level, and training a model that identifies the optimal relationship between feature inputs and the user state. While this approach carries merit, the number of levels that are practical to create and present to a human operator in a data collection session is very limited within reasonable time constraints. Furthermore, scientists typically make the assumption that a self-reported estimate of user state remains constant through a data collection trial, when it is highly likely there is variability in the operator's state throughout each trial. The ability to produce frequent real-time updates has also been limited because of the large time window of physiological data required to reliably detect a human operator's state. The most common practice has been to simply accept this limitation by scaling back the user state estimation update rate to one that produces acceptable accuracy.

BRIEF SUMMARY OF THE INVENTION

The following summary is included only to introduce some concepts discussed in the Detailed Description below. This summary is not comprehensive and is not intended to delineate the scope of protectable subject matter, which is set forth by the claims presented at the end.

Some embodiments of the disclosed user state estimation systems and methods provide a real-time, model-based classifier and predictor of user state on a continuous (in some embodiments, second-by-second), high resolution (0-100) scale.

In one example embodiment, a computer based method of estimating a user state is provided, the method comprising inputting a physiological measure into a user state estimation model and estimating a user state measure utilizing the user state estimation model.

In some example embodiments of the systems and methods to determine user state, a computer based method of estimating an user state is provided, the method comprising receiving a physiological measure, receiving a performance measure, receiving a situational measure, receiving a self-report measure, inputting the physiological measure, the performance measure, the situational measure and the self-report measure into a user state estimation model and automatically determine a real-time user state measure utilizing the user state estimation model.

In some example embodiments, a computer based method to estimate a user state is provided comprising receiving a plurality of first inputs at an intermittent interval, receiving a plurality of second inputs at a frequent interval, injecting a noise input into the plurality of first inputs at the frequent interval to create a plurality of enhanced first inputs whereby the plurality of enhance first inputs correspond to the plurality of second inputs at the frequent interval, inputting the enhanced first inputs and the plurality of second inputs into a state estimation model whereby a state can be estimated based on the plurality of second inputs and estimating the state based on the plurality of second inputs. In some embodiments, the noise input comprises physiological correlate for a user state. In some embodiments, the physiological correlate for a user state comprises a ratio of electroencephalogram (EEG) measures comprising a Frontal Midline Theta data over a Parietal Midline Alpha for the user state of a user workload. In some embodiments, the state estimation model comprises a relational database containing a weighted relationship of the plurality of second inputs to the plurality of first inputs. In some embodiments, the plurality of second inputs comprises a plurality of physiological inputs of a user and the plurality of second inputs comprises a plurality of state inputs of the user. In some embodiments, the plurality of first inputs comprises a self-reported data of the state of a user. In some embodiments, the plurality of first inputs comprises at least one self-reported user state rating. In some embodiments, the state estimate is made in a scale of 0-100. In some embodiments, the plurality of second inputs comprises at least one selected from a group comprising: a physiological measure, a performance measure and a situational measure. In some embodiments, the frequent interval is about a continuous interval.

In some embodiments, the methods further comprise receiving a baseline input as one of the plurality of first inputs.

In some embodiments, the methods further comprises inputting the enhanced first inputs and the plurality of second inputs into a machine learning model to create the state estimation model. In some embodiments, the machine learning model comprises an artificial neural network. In some embodiments, the artificial neural network is configured to find a mathematical relationship between a physiological feature and a state measurement.

In some embodiments, the methods further comprise receiving a plurality of enhanced actual first inputs and a plurality of actual second inputs, retraining the state estimation model with the plurality of enhance actual first inputs and the plurality of actual second inputs to create a retrained state estimation model and estimating the state based on the plurality of execution inputs. In some embodiments, the retraining comprises inputting a plurality of enhanced actual first inputs and a plurality of actual second inputs into a machine learning model to create the retrained state estimation model.

In some embodiments, a computer based method to estimate a state of a user is provided comprising receiving a plurality of first inputs at an intermittent interval, receiving a plurality of second inputs at a frequent interval, inputting the plurality of first inputs and the plurality of second inputs into a state estimation model whereby a state can be estimated based on the plurality of second inputs and estimating a future state of a user at a future time utilizing the state estimation model. In some embodiments, the methods further comprise injecting a noise input into the plurality of first inputs at the frequent interval to create a plurality of enhanced first inputs whereby the plurality of enhance first inputs correspond to the plurality of second inputs at the frequent interval and inputting the enhanced first inputs and the plurality of second inputs into the state estimation model whereby the state can be estimated based on the plurality of second inputs. In some embodiments, the methods further comprise modifying a user interface based on the future state of the user. In some embodiments, the step of modifying the user interface based on the future state of the user comprises eliminating an unnecessary information set from a user display and displaying a necessary information set based on the future state of the user.

In some embodiments, a computer based system for estimating a user state is provided comprising a processor and a non-transitory computer readable medium having a computer readable program code embodied therein, said computer readable program code configured to be executed to implement the methods to estimate a state.

In some embodiments, a computer program product is provided for estimating a user state comprising a non-transitory computer readable medium having a computer readable program code embodied therein, said computer readable program code configured to be executed to implement the methods to estimate a user state. Some example embodiments of the systems and methods to determine user state provide s use an adaptive layer in conjunction with multi-modal data source inputs to make predictions of user state and performance.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1:
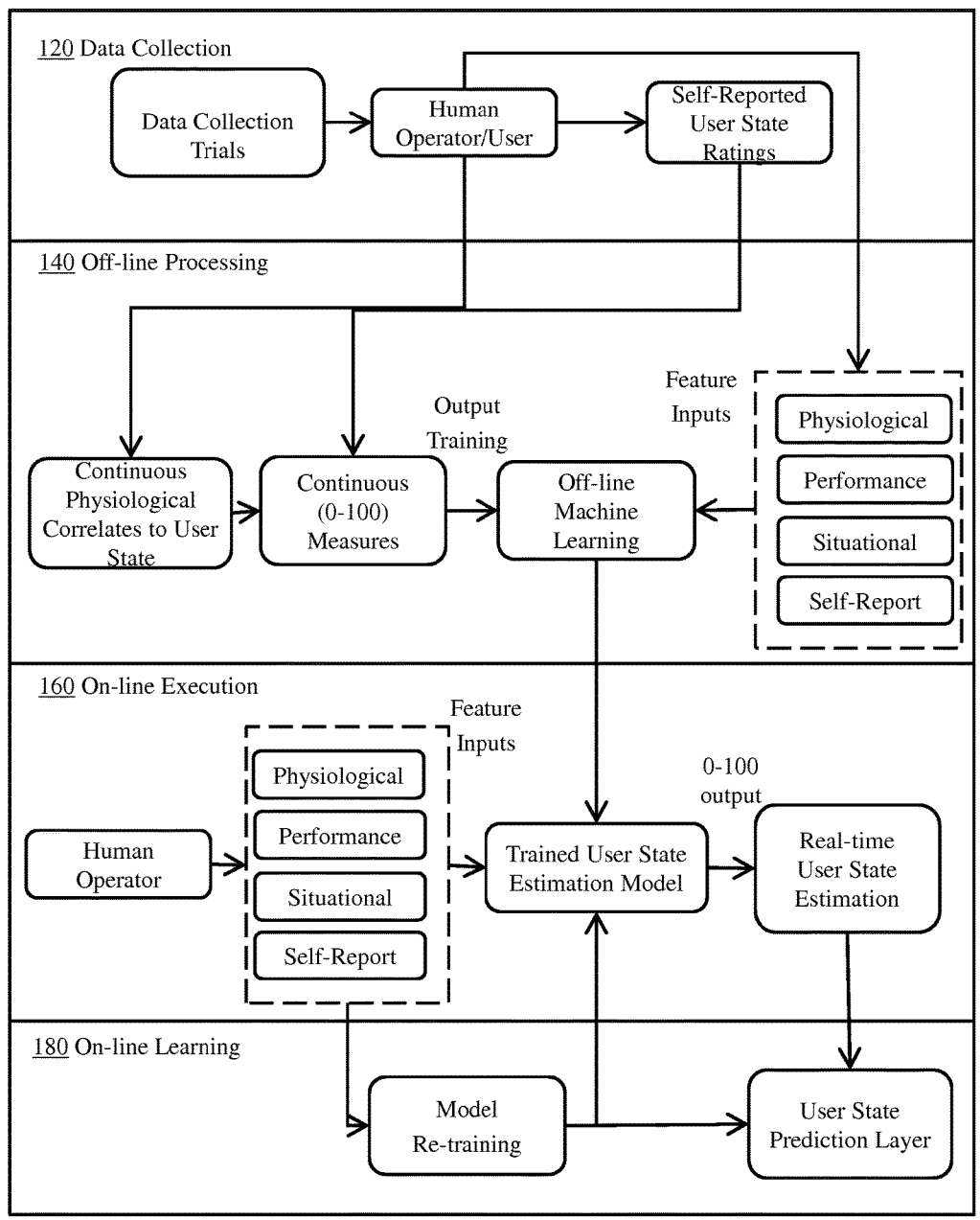
FIG. 1 shows an example process overview of the methods disclosed illustrating: (a) using physiological derived noise added to self-reported user state ratings; (b) multi-modal data source fusion to improve precision at frequent updates; and (c) on-line adaptation and prediction for human user state.

Systems and methods to determine a user state will now be described in detail with reference to the accompanying drawings. It will be appreciated that, while the following description illustrates concepts of the invention utilizing a system that determines the user state of a human operator of a system, the systems and methods disclosed herein have wide applicability. For example, the systems and methods described herein may be readily employed with embodiments of user states such as workload, task engagement, stress or trust. Notwithstanding the specific example embodiments set forth below, all such variations and modifications that would be envisioned by one of ordinary skill in the art are intended to fall within the scope of this disclosure.

As used herein, a state is representation of the condition of a person, a user or a thing to include a particular condition of mind or feeling of a person. A state may comprise one or more state types such as but not limited to user affect, user stress, user workload, user tasks engagement or user mental fatigue.

An alternative approach provided by the user state estimation systems and methods disclosed herein is to support the user state estimation by providing more precise decision aids by providing a real-time, model-based classifier and predictor of user state on a frequent and high resolution (e.g., 0-100) scale. This may be accomplished by applying machine learning methods, such as ANNs or SVMs, to train a state estimation model that identifies the best fit between one set of objective data input and more subjective user state inputs. With respect to training the state estimation model, noise may be injected into each subjective measurement for each corresponding trial to generate a user state estimate in intervals corresponding to the intervals the objective data input. Noise injection is used to provide a more frequent interval of state inputs which otherwise would be impractical, if not impossible, to obtain by asking for operator responses at more frequent intervals (e.g., once per five seconds). This more frequent granularity of data modeling allows for more granularities in the resulting state estimates. For example, noise can be added to self-reported workload ratings based on mathematical algorithms that process contextual data about the situation at each point in time to produce the direction and magnitude of noise. This algorithm design overcomes this limitation by adding physiological-based noise to self-reported user state ratings from the data collection environment. This noise is added by using a known physiological correlate for a particular user state (e.g., heart rate and workload) based on empirically derived relationships shown in published literature. While it is known that adding noise to data sets can produce some benefits to machine learning based models, typically the injected noise is intentionally random. Typically, physiological data is considered strictly as a feature input for the model, with the goal being to infer what a physiological signal means. The idea of applying a known physiological correlate to an input for training a model is contrary to the majority of trends being explored in this field of work.

Embodiments of disclosed user state estimation methods provide more frequent estimates of user state. The disclosed embodiments have shown promising accuracy using updates as frequently as once per second, whereas the majority of user state estimation algorithms that use physiological inputs produce updates every 60 seconds or greater. Typically the limitation with frequent output is the susceptibility to low model accuracy due to the lower volume of data collected in a small time window. The disclosed systems and methods overcome this limitation by its heavy use of multi-modal data sources (physiological, situational, task performance, and self-reported factors/measures) and retaining memory of each data source which greatly expands the volume of data available at any given time and seeks agreement across data sources. This more frequent modeling contrasts most user state modeling research using physiological data in real-time settings that traditionally focus on distinguishing between contrasting extreme levels (e.g., high versus low workload). This traditional approach does not require a high resolution model output, and hence the addition of noise to self-reported user state ratings is not necessary to generate traditional user state estimation algorithms. However, there are likely to be technologies or research communities that require user state estimations with higher resolution than simply high versus low.

Embodiments of disclosed user state estimation methods also benefit from the integration of multi-modal data sources—specifically physiological signals, task performance measurement, situational data/measures, and self-reported data/measures—to sustain acceptable accuracy at high frequency updates. This approach requires deep multidisciplinary expertise in each category of work, and few opportunities have emerged that enable this interaction of practitioner communities to occur. Furthermore, the majority of research conducted on physiological-derived user state estimates has sought to establish empirical relationships between physiological signals and a particular cognitive state. This approach differs in that it intends to find the optimal set of factors, physiological or not, to reliably estimate user state by applying findings from the existing body of research, rather than deriving these factors from new findings.

Embodiments of disclosed user state estimation methods are also able to provide a more generalized model across users. This generalization is difficult to achieve because of the difference of physiological signals across human beings and across time/days (e.g., differences in heart rate, EEG signals, etc.). Some solutions have demonstrated success with models that are trained specifically for a single person, however the requirement to train a model for all potential operators of a system can be very impractical and time consuming.

Embodiments of disclosed user state estimation methods may also be able to improve the accuracy of user state estimation algorithms by collecting baseline physiological data at the start of a session. Baseline collection ensures that physiological data are measured in relative terms for a particular human at a particularly time/day. The methods may apply an intelligent baseline assessment algorithm that adjusts the user state estimation weights based on a human operator's self-reported inputs at the start of a task performance session. Traditional baseline techniques do not use an adaptive weighting technique based on a wide variety of self-reported factors (e.g., antecedent lifestyle factors).

Some embodiments of the user state estimation systems and methods provide an on-line learning component of the disclosed user state estimation algorithm. This is different than approaches that attempt to obtain the highest possible accuracy for specific individuals by training a model for a specific person. These solutions do not typically adapt user state estimation algorithms to human operators using on-line methods, nor do they use this information to make predictions. The disclosed methods may adapt to a human operator in an on-line manner, using both intelligent baseline assessments and real-time weight adjustments to improve the precision of user state estimation without relying on a custom build model for a human operator. Furthermore, as a task performance session is in progress, an on-line learning component adapts the user state estimation weights according to the operator's physiological, performance, and self-report data in real-time.

This method also includes an approach for making predictions of the user state and its relationship to performance. Typical user state estimation approaches across scientific communities are focused on real-time estimates rather than predictive estimates. Predictions of an operator's state and performance are not traditionally associated with research on user state estimation algorithms. Predictions of an operator's state have also been unviable due to the lack of a high-resolution measure of user state that allows subtle trends and fluctuations to be monitored and modeled. And yet, predictions are helpful to facilitate the use of user state estimations for operational application, such as how or when to adaptively aid an operator's work.

Taken together, the disclosed approaches for user state estimation algorithm development incorporate the disclosed functions into a unified framework. Embodiments of the disclosed systems and methods of user state estimation provide for real-time, continuous, or high-resolution user state estimation using multi-modal data source inputs, on-line training, and predictive techniques.

One Embodiment of Methods to Determine User State:

To illustrate embodiments of the disclosed systems and methods to estimate a user state, a user state of "workload" is used to represent one type of user state. It is understood that embodiments of these systems and methods are capable of estimating other user states such as, but not limited to workload, task engagement, stress or trust.

Embodiments of the disclosed systems and methods utilize physiological-based user state modeling and classification techniques. The systems and methods include a flexible architecture for collecting and processing objective data such as physiological, behavioral, and situational data from disparate sources in real-time into a centralized location. The systems and methods utilize a machine learning based modeling approach that is trained from data sets spanning categories such as: Physiological, Self-reported factors, Performance, and Situational. The systems and methods are configured to estimate a user workload as a function of these categories. Given that workload has a relationship to task performance embodiments may be able to leverage frequent workload estimates as one basis for when and how to enhance task performance and aid the performance of the user.

For illustration purposes and not for limitation, FIG. 1 illustrates the functional steps of one example embodiment of user state estimation methods. This embodiment includes four general categories to operate this process. As shown, the methods may comprise the general tasks grouped under the categories of data collection 120, data processing 140, execution 160 and learning 180. Data collection 120 generally comprises the collection of objective and objective and subjective data inputs from a human operator/user that will be used by the systems and methods. Off-line processing 140 generally comprises receiving and processing the data inputs collected and relating them to create mathematical models of the inputs for machine learning algorithms to create a user state estimation model. On-line execution 160 generally comprises utilizing the state estimation model in an actual situation where the model can be used to estimate the state of the user based on actual data inputs. On-line learning 180 comprises further steps to improve and/or retrain components of the system or further steps to augment the systems or predict the future state of the user.

Figure 2A:
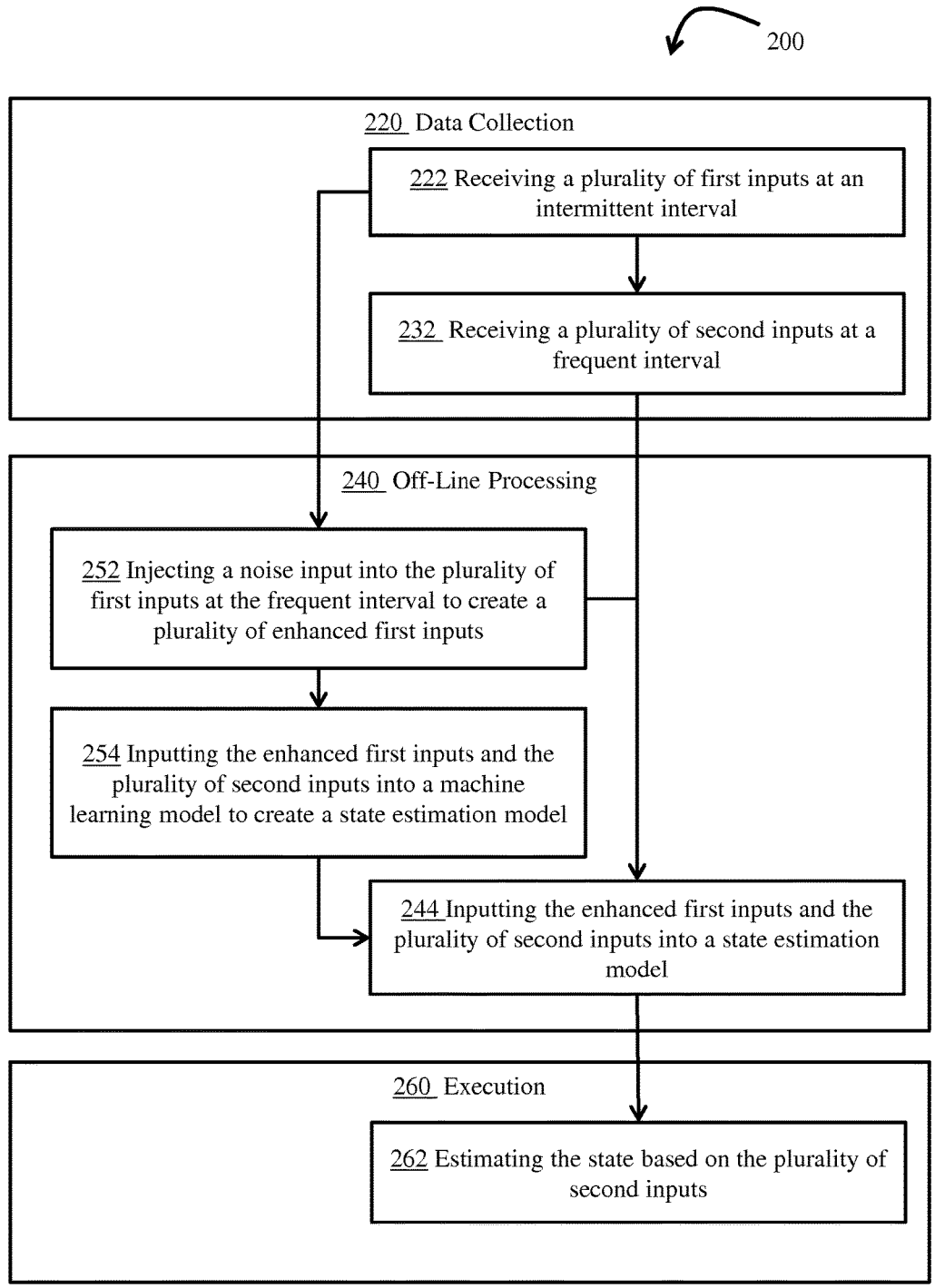
FIG. 2A is a process diagram illustrating one example embodiment of methods of estimating a user state.

Shown in FIG. 2A is a process diagram illustrating one embodiment of the methods of user state estimation. As shown, the method 200 generally includes the tasks of data collection at 220, off-line processing at 240 and execution at 260 as shown in FIG. 1. Shown in some more detail, the method 200 generally comprises a computer based method of receiving a plurality of first inputs at an intermittent interval at 222, receiving a plurality of second inputs at a frequent interval at 232, injecting a noise input into the plurality of first inputs at the frequent interval to create a plurality of enhanced first inputs at 252 whereby the plurality of enhance first inputs correspond to the plurality of second inputs at the frequent interval, inputting the enhanced first inputs and the plurality of second inputs into a state estimation model at 244 whereby a state can be estimated based on the plurality of second inputs and estimating the state based on the plurality of second inputs at 262. As shown, in some embodiments, the method 200 may further comprise inputting the enhanced first inputs and the plurality of second inputs into a machine learning model to create the state estimation model at 244.

In the embodiments disclosed, the plurality of first inputs at an intermittent interval may reflect those inputs that are difficult to obtain at a regular interval and may reflect more subjective measures. For example, a user state, such as a self-reported workload, may be the plurality of first inputs. The plurality of second inputs at a frequent interval reflect those inputs that may be more objective measure capable of being obtained at a more frequent interval, sometimes continuously and in real-time. For example, physiological, performance and situational inputs may be examples of the plurality of second inputs.

Referring to FIG. 2A, the data collection stage at 220 generally corresponds to the steps of 222 and 232. Once a type of state is selected for estimation, data collection trials are implemented to collect data within the task environment of interest associated with that type of state. A set of human user may participate in the trials while being attached to non-invasive physiological devices, thus allowing other categories of input to be collected (e.g., frequent interval inputs, physiological, performance or situational). The human users may also provide self-reported ratings of their state for each trial (e.g., intermittent interval inputs). The data collection trials may introduce a range of variability with regard to the user state. State variability may range from very low to very high. Each trial may focus on providing state values at intermittent intervals that may be used with the methods disclosed to sustain a frequent interval continuous level of the selected user state within the trial. For example, using a typical intended 0-100 output resolution, approximately 15 trials are suggested at a minimum; however more trials may be added precision to the extent it is practical.

In some embodiments, the collection of physiological measures (neurophysiological and psychophysiological) may comply with a Neuroergonomic Universal Architecture and may include a suite of neurophysiological and psychophysiological measures that will assess the state (e.g. workload) of the user with the goal of adapting the state estimation model, modifying a user interface or modifying controls to maximize performance of the user. To achieve this goal the architecture must contain signal processing components that will collect the raw biosignals from the operator and turn them into usable indices of user state (e.g. workload). Transforming neural and psychophysiological data into an informative cognitive or behavioral index involves several levels of signal processing: signal enhancement, data reduction, and signal analysis. The first level of processing can be thought of as signal enhancement, which is achieved by adjusting the amplification, filtering, sampling rate and recording period of the raw signal. This level of signal processing is typically integrated into the hardware and software used to collect the neural and psychophysiological data, and will vary depending on the signal being measured. For example, ECG signals are typically sampled at a rate between 500 and 1000 Hz using either a 60 Hz notch filter or a 35 Hz low pass filter. The second level of signal processing involves data reduction, which involves the distillations of large quantities of raw neural and psychophysiological signals into more manageable windows of data that can be subjected to further analyses. For example, when converting ECG recordings into measures of heart rate variability (HRV) the data are usually separated into windows of 60-120s to facilitate accurate analysis. This level of signal processing can either be done by a human operator or by additional software that is programmed to reduce a specific signal or set of signals. Once the data have been reduced they are then subjected to the third level of processing, signal analysis, which can include any number of processes, including statistical hypothesis testing, model fitting, and parameter estimation. For example, when using HRV as an index of parasympathetic nervous system activity, the raw EKG is "reduced" into windows of inter-beat-intervals (IBIs; the time between heart beats), which are then subjected to a frequency analysis (e.g. Fast Fourier Transform) to separate the low, mid, and high frequency components of the HRV signal. The high frequency component of HRV, or respiratory sinus arrhythmia (RSA), is then used as an index of parasympathetic nervous activity on the heart. It is also during this level of processing that signal classifiers can be used to differentiate between different levels or patterns of neural and psychophysiological activation that can be indicative of cognitive phenomena such as workload, stress or task engagement. Although the processes above are conceptually separated out into distinct levels of processing, the use of advanced neural and psychophysiological recording hardware and software enable the processing of most signals to occur in near real-time. The end product of signal processing is the ability to use one or more neural and psychophysiological measures to create inputs to create models that can identify an operator's state. These models may be created through the use of machine learning algorithms, or signal classifiers, that help discriminate between different patterns of neural and psychophysiological activity. Previous studies have attempted to use a wide range of methods for identifying patterns or trends in neural and psychophysiological data that could be associated with different levels of operator workload, including autoregressive statistical methods, stepwise discriminant analysis and ANNs.

The end product of the data collection stage is generally a set of temporally synchronized data representing both frequent interval data and intermittent interval data. The frequent interval data generally comprises data that is easily collected at a frequent interval. This type of data may comprise the physiological, performance and situational data. The intermittent data generally comprises data that is gathered intermittently due to the subjective nature of the data type or because the data is difficult to collect on a more frequent basis. This type of data may comprise the self-reported data related to the user state, such as user workload.

Referring to FIG. 2A, the second stage of the method 200 is off-line model processing generally shown at 240. In this stage, the inputs from data collection steps are used to train algorithms, such as machine learning algorithms, to build a state estimation model. The machine learning algorithmic approach may be any type of machine learning algorithm such as but not limited to Artificial Neural Networks (ANNs) or Support Vector Machines (SVMs). The inputs, as model training sets, are prepared in a manner consistent with the machine learning approach being employed. The inputs also include injecting noise into inputs taken at an intermittent interval to create enhanced inputs at 252 so that the intermittent interval inputs correlate more closely to inputs with a more frequent interval. The injection of noise into the intermittent interval inputs adds a higher resolution to these intermittent inputs for the machine learning approach to train against. Noise may be injected in data inputs according to a noise injection algorithm. The noise injection algorithm may comprise any type of noise to provide a more frequent data input for input such as the intermittent inputs to create enhanced inputs. In some embodiments, the noise injection algorithm may utilize a relationship of a known physiological correlate and inject it into the user state self-report ratings for each trial to try to create a more frequent, and in some embodiments a continuous, physiological metric of workload. As used herein, a physiological correlate is a type of data that is measured from a human operator's body (physiological) signals that has been shown through empirical research to have a known mathematical relationship to one or more human user states. For example, there may be a correlation between heart rate (as a physiological correlate) and workload (e.g., as workload increases, heart rate increases by some magnitude). As another example, there may be a correlation between Frontal Midline Theta (FZ Theta) (as a physiological correlate) collected via EEG and task engagement (e.g., as engagement lowers, FZ Theta power decreases). In one example embodiment of injecting noise, we inject a known physiological correlate to the self-report value for a corresponding period of time utilizing the noise injection algorithm. In this example, a ratio of 2 EEG data features is used as the source of noise injection: Frontal Midline Theta (Fz Theta) over Parietal Midline Alpha (Pz Alpha) which has been shown to have a strong correlation with operator workload. In this example, the noise injection algorithm receives a self-report value of workload as the input, injects the noise to this value on a second-by-second basis based on the Fz Theta/Pz Alpha ratio, and produces an output of a continuous second-by-second measurement of workload for the specified time period. In some embodiments, the systems and methods automate the process of injecting noise in a real-time user using a person's self-report entries as the start trigger for the algorithm. At this point, the inputs of the intermittent inputs have been enhanced with noise so that they are temporally related to the more frequent inputs. For example, the physiological, performance and situational inputs are synchronized with the self-reported state inputs that have been enhanced with the noise inputs. In some embodiments, the enhanced self-reported state inputs may be spread across a user state measure on a 0-100 scale. At 254, these feature inputs may then be fed into the machine learning algorithm so that an optimal fit can be determined to correlate the enhanced intermittent inputs to the frequent inputs. In one example embodiment of a machine learning algorithm, consistent with the example of injecting noise as described above, we apply an ANN algorithm to find a mathematically optimal relationship between (1) a large set of physiological features and (2) the frequent measurement of workload. In this example application, the feature set consists of EEG signals from 6 electrode sites on the scalp, interbeat interval (IBIs) derived from ECG and pupil diameter metrics.

Figure 3:
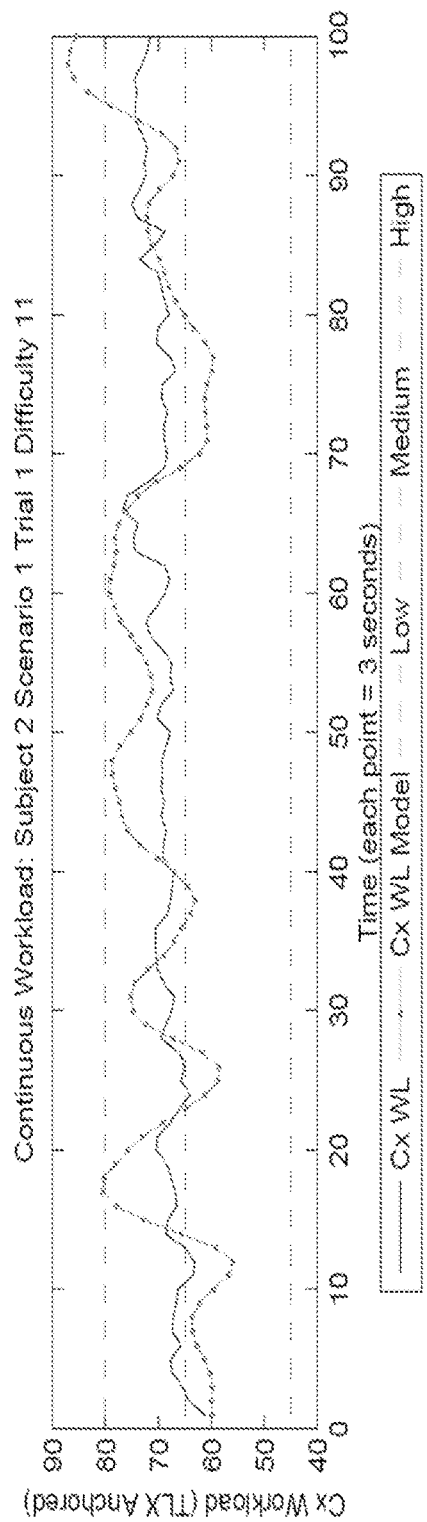
FIG. 3 illustrates the results of a self-reported user state rating with physiological noise added over a time period and a user workload estimate produced from multi-modal data source fusion over the same time period.

The result of the off-line processing stage is a fully trained state estimation model of the enhanced intermittent interval inputs given the frequent interval inputs. For example, the output of the machine learning process may be a state estimation model comprising a set of mathematical weights for each data feature in the feature set, contained in the format of a dynamically linked library (DLL) file (though other example applications might use different file formats). An example result of this off-line model processing stage is illustrated in FIG. 3 which shows a continuous estimate of operator workload with EEG-injected noise, and overlaid on this graph is a neural network's attempt to find the optimal fit with this measure on a second by second basis. FIG. 3 illustrates the result of a trained model of operator workload as a neural network attempts to find the best fit between a set of feature inputs and a continuous measure of self-reported workload with physiological noise added.

Referring back to FIG. 2A, a third stage of the method 200 is model execution shown at 260. In this stage, a human operator performs in the targeted task environment—ideally the same task environment in which the model was trained—while the user state model receives real-time data inputs via a data aggregator that performs data reduction. The categories of data (e.g., physiological, performance, situational, self-report) are collected and supplied to the state estimation model. At 262, the user state estimation algorithm uses the trained weights to determine an estimate of the operator's state in real-time and with high frequency updates (e.g., once per second).

Referring to FIG. 1, an optional fourth stage of these methods may include on-line learning 180. In this stage, the state estimation model may be re-trained and adapt its weights for each feature input based on the pattern of data being received from the current human operator. This stage may also include a predictive layer for the user state and performance based on historical inputs. This stage is captured in greater detail in FIG. 2. For the prediction layer, we found more successful results with Support Vector Machines (SVMs).

Figure 2B:
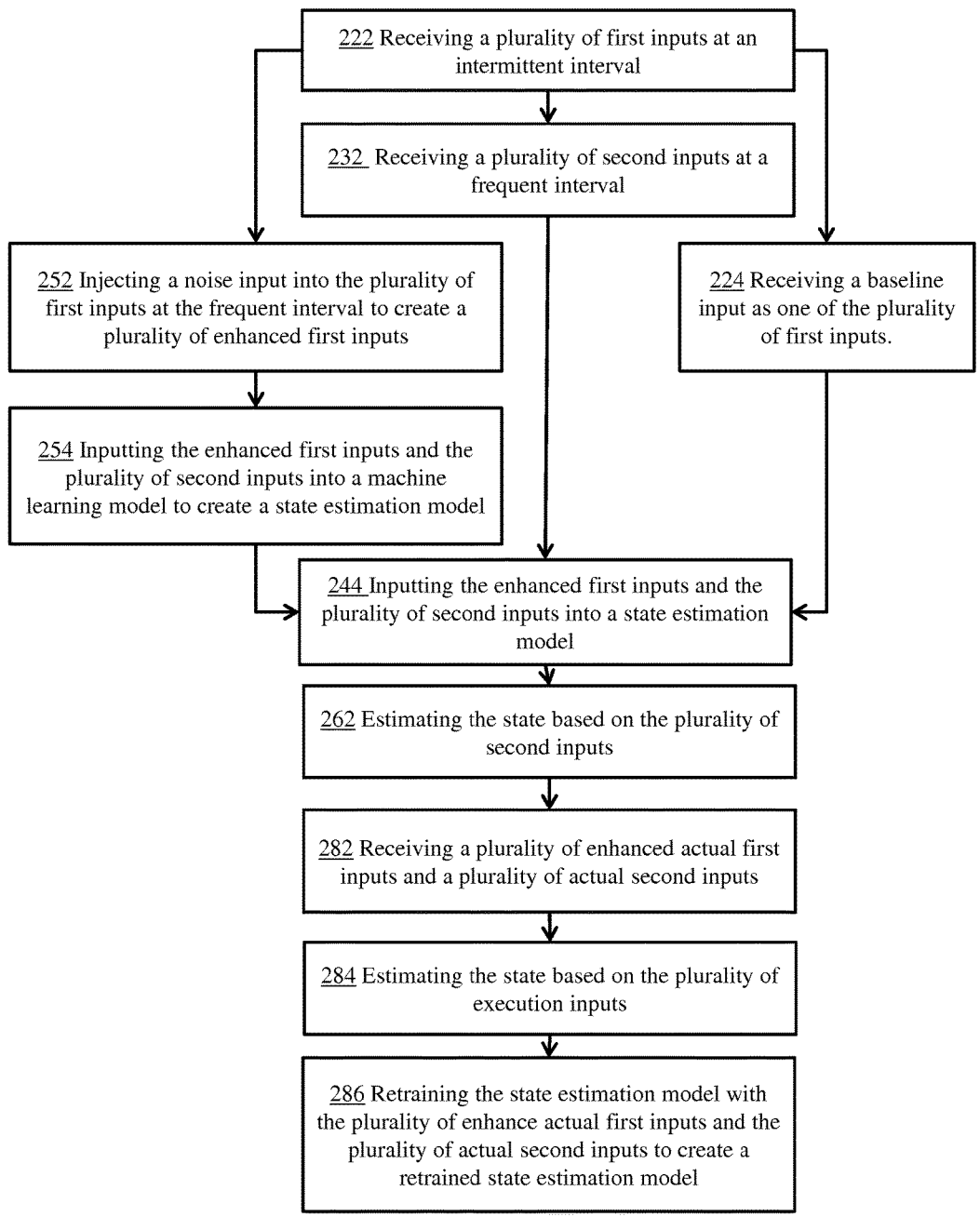
FIG. 2B is a process diagram illustrating another example embodiment of methods of estimating a user state.

FIG. 2B illustrates an embodiment incorporating on-line learning tasks. As shown, these methods may further comprise receiving a plurality of enhanced actual first inputs and a plurality of actual second inputs at 282, estimating the state based on the plurality of execution inputs at 284 and retraining the state estimation model with the plurality of enhance actual first inputs and the plurality of actual second inputs to create a retrained state estimation model at 286. With the retrained model, the state may be estimated based on the plurality of execution inputs. In some embodiments, the retraining comprises inputting a plurality of enhanced actual first inputs and a plurality of actual second inputs into a machine learning model to create the retrained state estimation model.

This on-line model retraining may be able to improve the precision of the user state estimation across different individuals over time. The on-line retraining process may be triggered by a scalable set of operator-driven inputs dependent on the state being modeled. In some of these embodiments, the scale of these inputs is set to consume the lowest possible time, effort, attention, and frequency of input from the operator (e.g., 5-second response per every 30 minutes). Using this trigger, a set of sub-components may dynamically update the model weights using the operator input data in conjunction with recent physiological, behavioral, and situational data that has occurred during a corresponding timeframe, resulting in more accurate and individualized estimate of user state that improves over time without the need for prior custom-built classifiers for each human operator.

FIG. 2B also illustrates at 224, embodiments of user state estimation methods that may receive a baseline input as one of the plurality of first inputs.

Further Embodiments of User State Estimation Methods:

Referring again to FIG. 1, the predictive methods may utilize memory of historical data to help facilitate informed, and proactive, augmentation decisions based on predict user state. The predictive accuracy is dependent on the level of granularity and update frequency of the real-time user state classifier. For example, workload estimates on a 0-100 scale and updated once per second allows a trained model to monitor subtle trends and changes not otherwise possible with highly discrete classifiers (e.g., high versus low); this may potentially be the difference between knowing when, and when not, to intervene with an augmentation strategy. In addition, forecasted knowledge of the situation—such as when a highly tactical and attention-demanding phase of a mission is known to occur—is valuable, if not essential, context that adds to the accuracy of workload and performance predictions.

In some of these embodiments, by estimating a future state of a user, the methods may further comprise modifying a user interface based on the future state of the user. This modification may be used to augment the system the user is operating. For example, rather than providing a user interface that results in a fixed presentation of information throughout the entirety of the human-computer interaction, recognizing that the human user states (e.g. workload, situational awareness, and affect) are dynamic and ever-changing, an embodiment is provided that continuously monitors the human state via sensors, such as neural and psychophysiological sensors, so that the interface could be adapted to accommodate the current state. For instance, if the computer detects that the human operator is experiencing high workload, as in the case of an RPA pilot monitoring a video feed while at the same time navigating a ground vehicle and communicating with the base commander, it would make changes to the interface that will result in (1) elimination all the unnecessary/extra information that may clutter the display and increase the work load demand, and (2) bringing into focus central information that needs attention. Some adaptive augmentation systems would be able to incorporate predictions of user state and its expected impact on human performance. Predictive capabilities would provide an invaluable tool for proactively address problems before they occur.

To perform the step of estimating future states of a user at a future time, a prediction (layer) algorithm may be utilized. For example, one embodiment may utilize historical measurements from the state estimation model—e.g., each second by second workload estimate over the past 60 seconds—and uses the machine learning approach of SVMs to find an optimal mathematical relationship to the state estimation outputs that occurred in the future (e.g., the workload estimate measure 30 seconds into the future, relative to a set of values).

Figure 4:
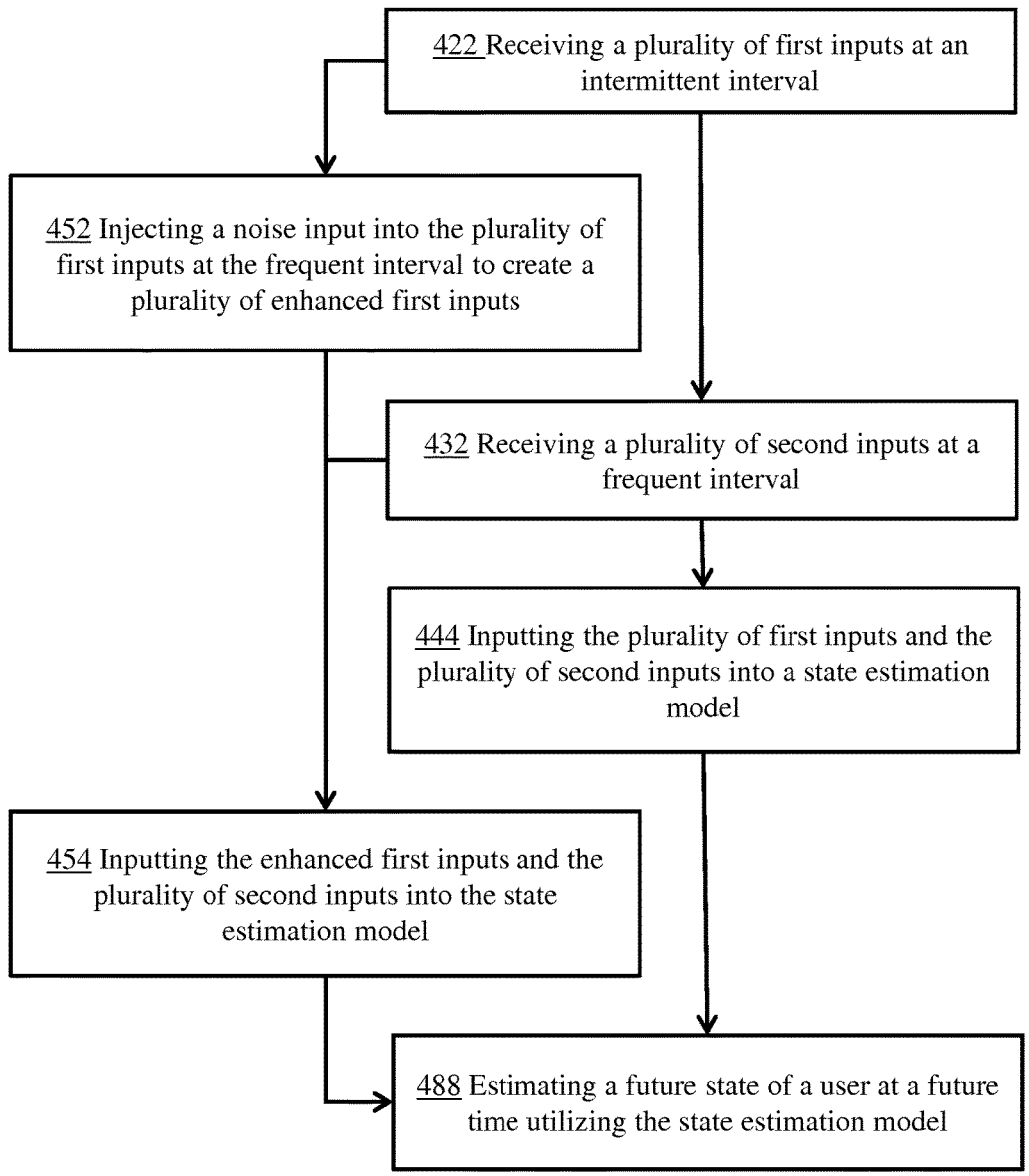
FIG. 4 is a process diagram illustrating an example embodiment of methods of estimating a user state, here estimating a future state.

FIG. 4 illustrates another example embodiment of user state estimation systems and methods. As shown, the methods may comprise receiving a plurality of first inputs at an intermittent interval at 422, receiving a plurality of second inputs at a frequent interval at 432, inputting the plurality of first inputs and the plurality of second inputs into a state estimation model at 444 whereby a state can be estimated based on the plurality of second inputs and estimating a future state of a user at a future time utilizing the state estimation model at 488.

Consistent with the other methods disclosed, in some embodiment, the method 400 may further comprise injecting a noise input into the plurality of first inputs at the frequent interval to create a plurality of enhanced first inputs at 452 whereby the plurality of enhance first inputs correspond to the plurality of second inputs at the frequent interval and inputting the enhanced first inputs and the plurality of second inputs into the state estimation model at 454 whereby the state can be estimated based on the plurality of second inputs.

In some embodiments other on-line learning methods may be able to augment the performance of the user. For example, once user state is appropriately measured, cognitive modeling approaches may be able to drive mitigation strategies that will help operators in maintaining an optimal functional state and hence performance. These approaches may include recommendations for resource re-allocation, automated aids or dynamically managing excessively low or high levels of workload and stress. Covering the range of factors that might contribute to user state benefits from a meaningful integration of various psychophysiological and behavioral measures, and the accurate and reliable assessment of user state may also take into account performance on mission tasks. Psychophysiological and system-based performance measures (e.g., time on target, airframe flight characteristics) can be used to inform one another through meaningful integration. Some embodiments may estimate user and/or team state for the purpose of resource re-allocation of adaptive aiding.

In some embodiments, determining adaptive automation strategies may be performed by evaluating in real-time the variety of data collected during an user's mission and determining whether the level of aid to the user in any of the stages of information processing should be changed, i.e., in line with a levels of automation approach. In this scenario, a cognitive model may (1) read in and classify both neuro/physiological and system-based performance measures, (2) further integrate the data with knowledge of the tasks and mission, and (3) inform an adaptive aiding system of the current user state and estimates of future user state.

One example embodiment of a cognitive model designed for adaptive automation may comprise utilizing a Hidden Markov Models (HMM). One purpose of this type of model is to alert the adaptive aiding system when conditions are right for an aid to be turned on or off utilizing a stochastic model of user state evolution, informed over time by the observed multi-source measures. A HMM approach may represent and identify user state dynamics. HMM are an extension of Markov Models in which the observations are probabilistic functions of the (hidden) true system state that therefore allow for identifying and tracking user state over time in the presence of large information gaps. In one embodiment, a limited, discrete set of possible user states may be defined, in coordination with the need to understand the stages of information processing as they are executed (see FIG. 5A). To extend the capabilities of that embodiment, an assumption that the information processing stages for different scenario event are independent should be relaxed. Below is a discussion of an example embodiment of a method to relax that assumption.

Let the set of individual states be represented as $S=\{s_1, s_2, \ldots, s_N\}$ and let the true system state at time t be $x_t$. Additionally, let M be the number of possible observations that can be obtained at any given time so that the set of feasible observations is $V=\{v_1, v_2, \ldots, v_M\}$, and at time t we obtain a measurement (observation) $o_t$. Note that each observation can consist of multiple measurements or features. The HMM is defined by specifying the state dynamics process, an observation process, and the prior information. The state dynamics process is represented as a probabilistic state transition graph, in which we define the state transition probability distribution:

$A=\{a_{ij}\}$, where $a_{ij}=P(x_{t+1}=s_j|x_t=s_i)$, $1 \le i, j \le N$

In the above, $a_{ij}$ is the probability that the user state will change to $s_j$ given that it is currently in state $s_i$. The observation process is represented as a stochastic signal generated using conditional observation probability distribution:

$B=\{b_j(m)\}$, where $b_j(m)=P(o_t=v_m|x_t=s_j)$, $1 \le j \le N$; $1 \le m \le M$.

Here, $b_j(m)$ is a probability that the observation $v_m$ is obtained while the state of operator is $s_j$. The prior information is represented as a belief about the initial state of the operator:

$\pi=P(x_0=s_i)$, $1 \le i \le N$.

Here, $\pi_i$ is a probability that the initial state of the operator is $s_i$. As the result, we can represent an HMM as a tuple:

$\mu=\{A,B,\pi\}$.

Figure 5A:
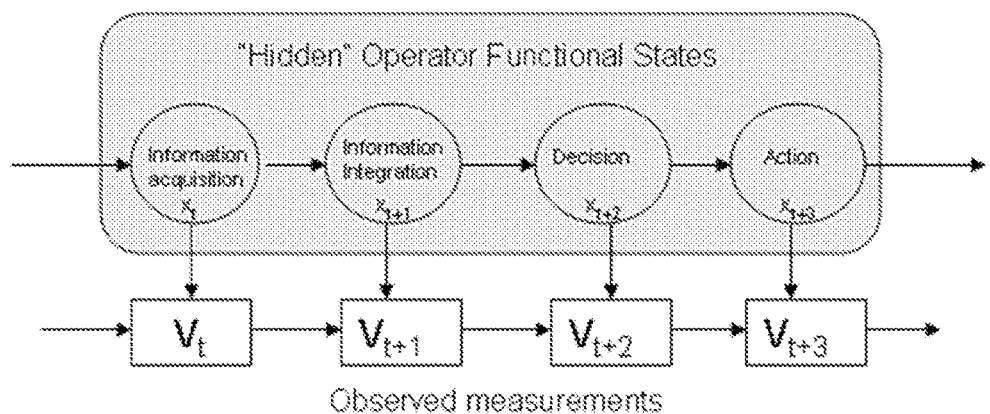
FIG. 5A shows an example embodiment of a model used to augment a user based on user workload.

As shown in FIG. 5A, our observations of the system, in the form of the measures to be developed, are generated by the underlying user state. We then use these observations to solve the problem of discovering which of the possible underlying states is most likely to have produced what we observed at any given time. This information together with additional contextual information drives recommendations to the adaptive aiding system. Consider, for example, a scenario in which the primary task is eliminating enemy tanks in a Suppression of Enemy Defenses (SEAD) mission. During a specific period during the scenario, four tanks appear simultaneously. This information is used to signal the start of the Information Acquisition stage of information processing for each tank. Four HMMs are initialized to track information processing associated with each tank, and specified contextual information is used by the model to signal progression of information processing for any of the tank HMMs. Tracking information processing stages allows for the identification of possible causes of changes in performance and workload, thereby allowing for the selection of the appropriate adaptive aid for each time period. Essentially, the model extracts performance, psycho/physiological, and contextual data from the PM Engine and can use this information to select the appropriate aid to be integrated into the user interface. For example, if the decrease in performance or increase in workload occurs mainly in the Decision Selection stage of the recent tasks, this would signal the user interface to present the operator with an automated aid which supports this stage of information processing. In this case, one potential aid which can be presented to the operator is a weapons-target pairing assignment matrix representing feasible actions. Additional information such as task priorities and processing times to determine the value of including them in the notion of user state may also be used. A potential extension to this model addresses the current assumption that the progress of an operator through the four stages of information processing required for each event will be independent of the 4-stage processes for other events. This assumption may simplify the problem for the preliminary instantiation of the model.

Figure 5B:
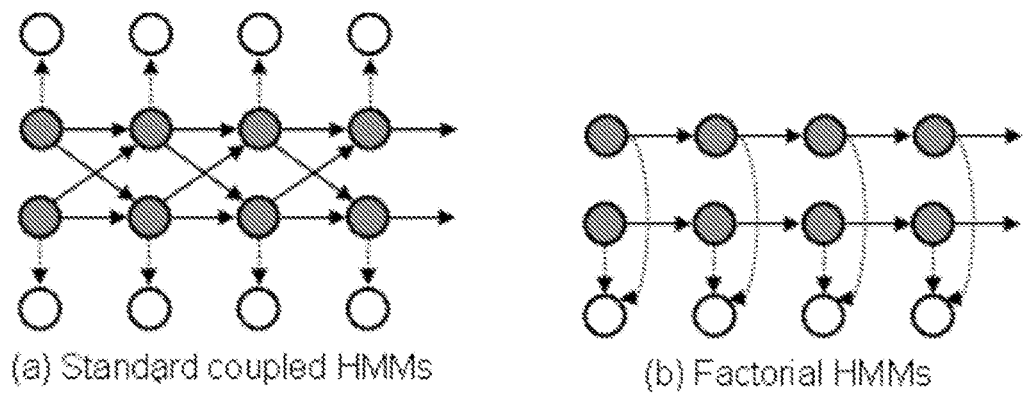
FIG. 5B shows another example embodiment of a model used to augment a user based on user workload.

In FIG. 5B(a), standard coupled HMM models are illustrated. These capture the dependencies of multiple processes (e.g., activities) on each other, while the observations could be decoupled to belong to one of the HMMs. These models can be used to represent how the activities of a single operator in prosecuting multiple targets depend on each other, while the observations might be well distinguishable to the target class tagged events. FIG. 5B(b) shows the structure of factorial HMMs, where multiple processes (activities) combine in producing the observations. This is especially needed in situations in which operators communicate, make decisions, plan and engage multiple targets at the same time. While these HMMs allow richer behavior modeling, their solutions are also more complex than standard HMMs. However, several efficient algorithms have been developed that are tailored to specific HMM architectures and can be used to enhance the model described above.

Another example embodiment of a cognitive model designed for adaptive automation may comprise moving beyond using the HMMs in isolation. This embodiment may comprise enhancing the system by combining methods of the control decisions of the adaptive aiding system into a single system implemented using a Partially Observed Markov Decision Process (POMDP). The POMDP adds a notion of control action to the HMM representation that will allow influencing or completely changing the current or future states and/or dynamics model of the operator. In addition, POMDP introduces the notion of the cost of control action and the reward (penalty) of reaching certain states, and obtains a control policy to maximize the expected total reward obtained over time. This may provide a unified representation of the expected effect of the control actions on user state into the decision process.

One Embodiment of the System to Determine User State:

Components of the system to determine user state may include custom code built in a modeling program such as MatLab. For illustration purposes and not for limitation, system components capable of implementing this user state estimation algorithm process are as listed below.

A task environment similar to that which the final model will be applied. The human operator conducts work in this task environment for both data collection and model execution stages of the process.

A self-report data entry software tool for the human operator's inputs of user state for each trial. Results from this tool are stored in a database for post-hoc retrieval.

Physiological sensors of interest, such as EEG, heart rate, and eye tracking. Results from these sensors are stored in a database for post-hoc retrieval.

Data listeners for each data source in the task environment (e.g., simulator, keystroke logger, physiological sensors, self-report software tool).

Machine learning software that is capable of employing the preferred machine learning approach. Any software application capable of training models using machine learning methods is suitable. For example only, a suitable software application that is capable of training models using machine learning methods includes a program called NeuroSolutions that is used for applying neural network training approaches. Custom built/non-commercial software application can also be used.

Data aggregation software for reducing each data source feature input into a normalized rate for the user state estimation algorithm.

Performance measurement software that calculates data from the task environment and from operator interactions to automatically decipher performance as a feature input to the user state estimations. Any software application capable of measuring performance is suitable. For example only, software sold by Aptima, Inc. of Woburn Mass. under the title of A-Measure software is suitable, specifically the PM Engine, SPOTLITE, and A-Measure database components.

Real-time task difficulty model component that can serve as a feature input into any user state model. In some embodiments, the task difficulty estimation component may be an implementation of a machine learning algorithm such as, but not limited to Support Vector Machines (SVMs) and in some embodiments, this component may be implemented as an Artificial Neural Networks (ANNs).

Real-time user state classification component based on the user state estimation values from the algorithm. This component is used to execute, in real-time, the model trained by the machine learning methods. In one embodiment, the user state classification and prediction components may use Artificial Neural Networks (ANNs).

Prediction model components for the user state and for task performance. The prediction model component is a software-based component that is used to execute, in real-time, the model trained by the machine learning methods (e.g. ANN).

Software module for executing real-time model training and adjusting the user state estimation algorithms weights in real-time.

A visualization dashboard for displaying all numerical inputs and outputs to and from the user state estimation algorithm.

Figure 7:
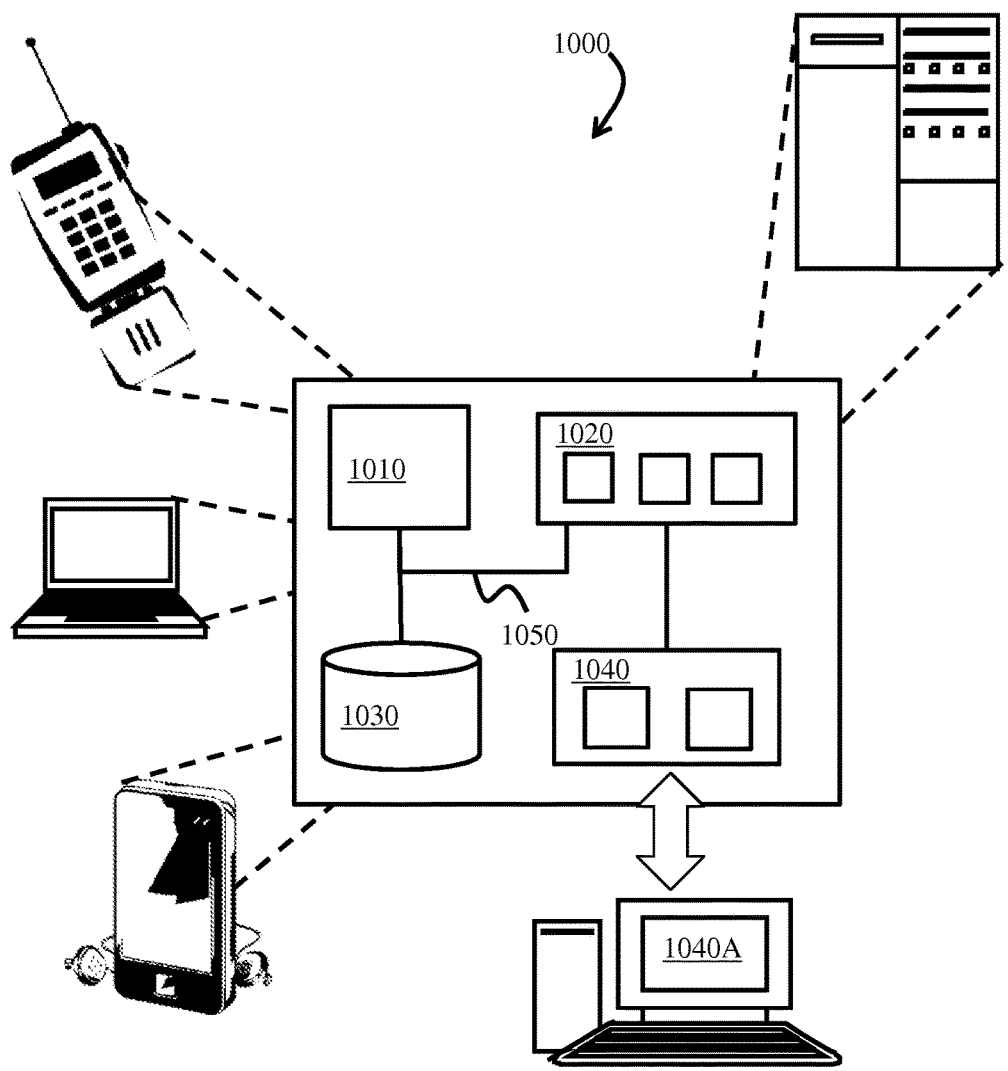
FIG. 7 shows a functional diagram of one embodiment of a suitable computer system.

The various method embodiments of the dynamic process modeling assembly will be generally implemented by a computer executing a sequence of program instructions for carrying out the steps of the methods, assuming all required data for processing is accessible to the computer, which sequence of program instructions may be embodied in a computer program product comprising media storing transitory and non-transitory embodiments of the program instructions. One example of a computer-based dynamic process modeling assembly is depicted in FIG. 7 herein by which the method of the present invention may be carried out. One embodiment of the assembly includes a processing unit, which houses a processor, memory and other systems components that implement a general purpose processing system or computer that may execute a computer program product comprising media, for example a compact storage medium such as a compact disc, which may be read by processing unit through disc drive, or any means known to the skilled artisan for providing the computer program product to the general purpose processing system for execution thereby.

The computer program may also be stored on hard disk drives within processing unit or may be located on a remote system such as a server, coupled to processing unit, via a network interface, such as an Ethernet interface. The monitor, mouse and keyboard can be coupled to processing unit through an input receiver or an output transmitter, to provide user interaction. The scanner and printer can be provided for document input and output. The printer can be coupled to processing unit via a network connection and may be coupled directly to the processing unit. The scanner can be coupled to processing unit directly but it should be understood that peripherals may be network coupled or direct coupled without affecting the ability of workstation computer to perform the method of the invention.

As will be readily apparent to those skilled in the art, the present invention can be realized in hardware, software, or a combination of hardware and software. Any kind of computer/server system(s), or other apparatus adapted for carrying out the methods described herein, is suited. A typical combination of hardware and software could be a general-purpose computer system with a computer program that, when loaded and executed, carries out the respective methods described herein. Alternatively, a specific use computer, containing specialized hardware for carrying out one or more of the functional tasks of the invention, could be utilized.

The present invention, or aspects of the invention, can also be embodied in a computer program product, which comprises all the respective features enabling the implementation of the methods described herein, and which, when loaded in a computer system, is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or reproduction in a different material form.

FIG. 7 is a schematic diagram of one embodiment of a generic computer system 1000. The system 1000 can be used for the operations described in association with any of the computer-implemented methods described herein. The system 1000 includes a processor 1010, a memory 1020, a storage device 1030, and an input/output device 1040. Each of the components 1010, 1020, 1030, and 1040 are interconnected using a system bus 1050. The processor 1010 is capable of processing instructions for execution within the system 1000. In one implementation, the processor 1010 is a single-threaded processor. In another implementation, the processor 1010 is a multi-threaded processor. The processor 1010 is capable of processing instructions stored in the memory 1020 or on the storage device 1030 to display information for a user interface on the input/output device 1040.

The memory 1020 stores information within the system 1000. In some implementations, the memory 1020 is a computer-readable storage medium. In one implementation, the memory 1020 is a volatile memory unit. In another implementation, the memory 1020 is a non-volatile memory unit.

The storage device 1030 is capable of providing mass storage for the system 1000. In some implementation, the storage device 1030 is a computer-readable storage medium. In various different implementations, the storage device 1030 may be a floppy disk device, a hard disk device, an optical disk device, or a tape device.

The input/output device 1040 provides input/output operations for the system 1000 and may be in communication with a user interface 1040A as shown. In one implementation, the input/output device 1040 includes a keyboard and/or pointing device. In another implementation, the input/output device 1040 includes a display unit for displaying graphical user interfaces.

The features described can be implemented in digital electronic circuitry, or in computer hardware, firmware, software, or in combinations of them such as but not limited to digital phone, cellular phones, laptop computers, desktop computers, digital assistants, servers or server/client systems. An apparatus can be implemented in a computer program product tangibly embodied in a machine-readable storage device, for execution by a programmable processor; and method steps can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a computer program of instructions include, by way of example, both general and special purpose microprocessors, and a sole processor or one of multiple processors of any kind of computer. Generally, a processor will receive instructions and data from a read-only memory or a random access memory or both. The elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube), LCD (liquid crystal display) or Plasma monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

Figure 8:
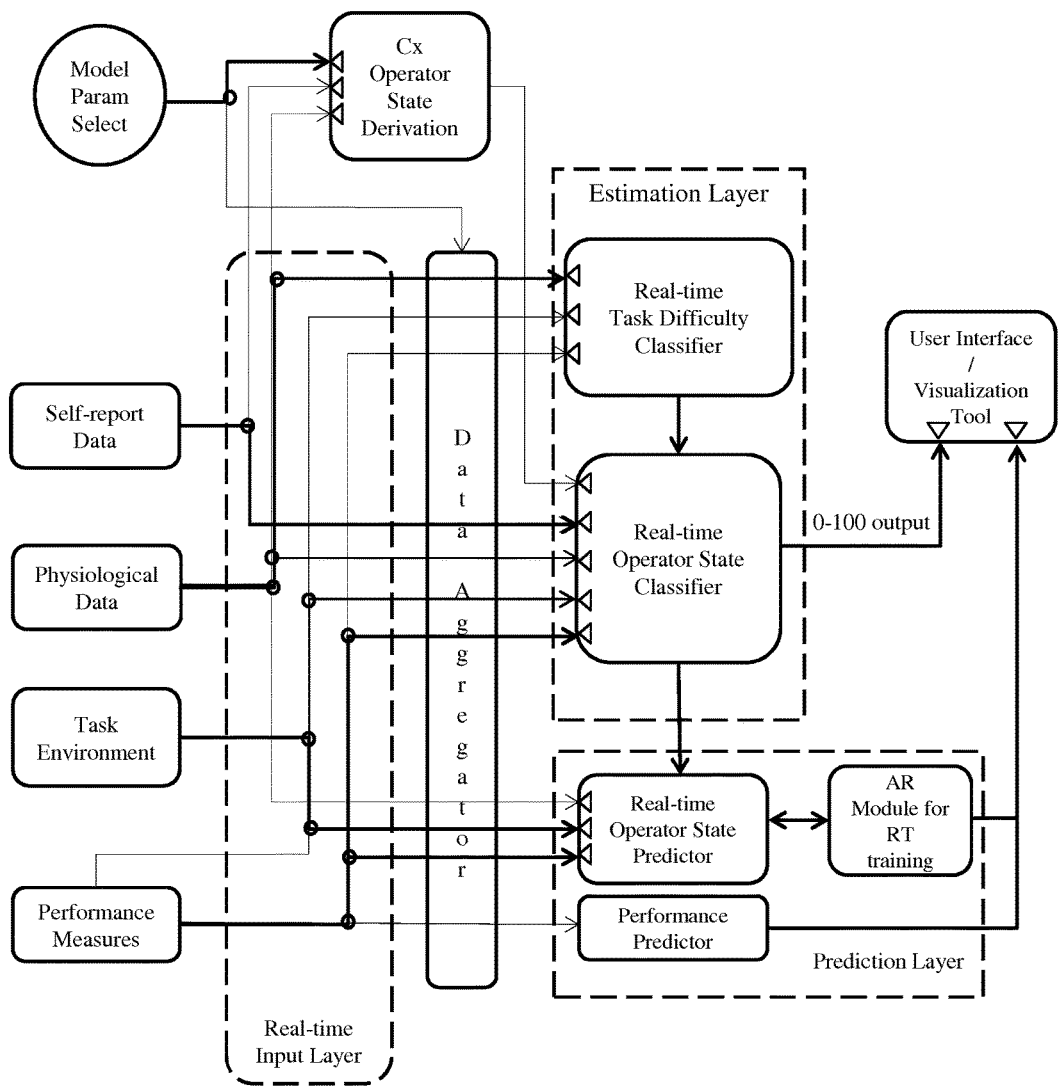
FIG. 8 shows a functional diagram of an example embodiment of an architecture for executing the user state estimation algorithm components.
Figure 9:
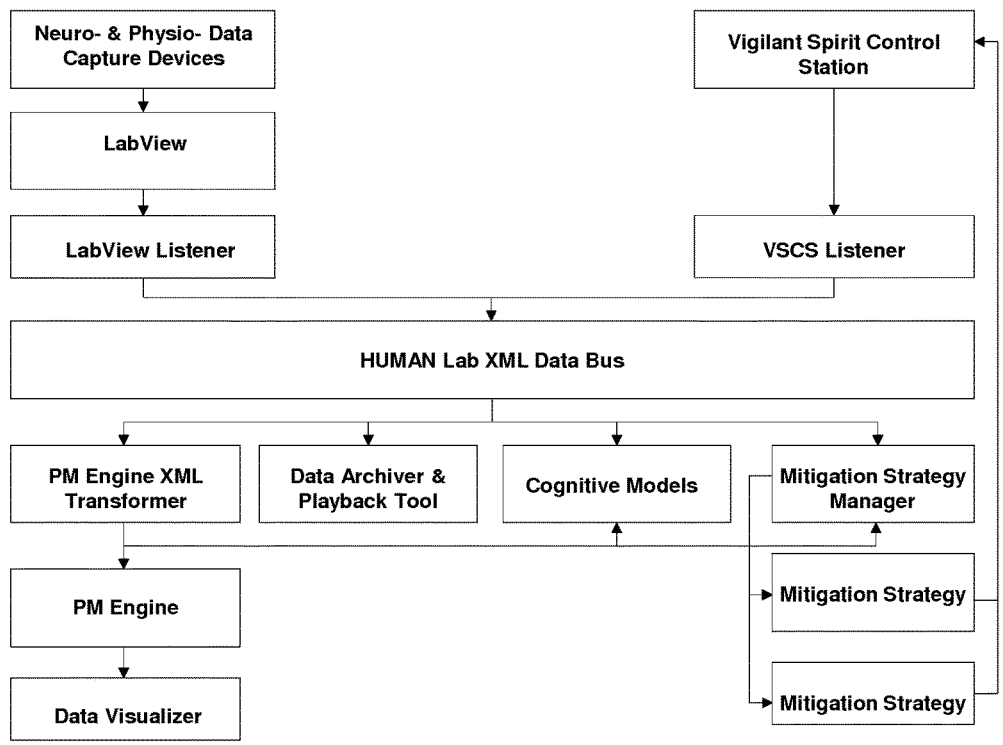
FIG. 9 shows a functional diagram of an example embodiment of a user state estimation system components integrated into an example learning management system.

A functional diagram of one embodiment of the computer program capable of executing the described methods is shown in the functional diagram in FIG. 8. This model architecture is designed to output continuous measures which are derived based on theoretically grounded physiological and/or behavioral correlates of a particular user state of interest. This architecture is designed to represent a user's functional state as it is influenced and indicated by multiple factors and data sources/inputs. Furthermore, the model is adaptive and developed to output and predict measures on a configurable second by second basis which may be used to represent an individual's perception on a 0-100 scale. This architecture is comprised of two layers (estimation and prediction layers) of machine learning-based models each serving a particular function. In one embodiment, the estimation and prediction layers consist of time-delay neural network (TDNN) models which will provide continuous real-time estimates and predictions of user state and performance across a configurable prediction horizon. The estimation layer provides second by second estimates of operator functional state which generates a time series to support real-time prediction within the model architecture's predictive layer. TDNN models are a common type of temporal supervised network. These models have memory components which serve to store historical values of the data passed through the network and provide the network with processing abilities to learn relationships in data over time. Machine-learning algorithms can account for model uncertainty and adapt to individuals over time. This increases user state classification accuracy within the real-time data acquisition setting.

This user state estimation process may work for virtually any functional state of interest and in any task environment that can accommodate the required hardware and software connections. Thus far, we have applied this process to the functional state of human cognitive workload and within the remotely piloted aircraft (RPA) task domain.

While in data collection mode to initiate this process, the task environment, physiological sensors, self-report data entry software tool, performance measurement software, and data listening components must all be active. All of these components may collect data for training the machine learning components of the user state estimation algorithm.

While in off-line training mode, only commercial software for executing the preferred machine learning approach is required. The machine learning portion imports the data sets collected during the data collection stage.

While in model execution mode, all of the same data sources (task environment, physiological sensors, self-report data entry, performance measurement software, and data listening components) must be active and available for real-time model consumption. There is also a data aggregation software module so that each data source is translated into a common format and input rate for the algorithms. Each component of the algorithm—the real-time task difficulty model, user state classification component, prediction model component, and on-line training module—runs in parallel by receiving data from the data aggregation module. Each of these module outputs can be displayed on the data visualization software module. As shown in FIG. 8, the task difficulty model is a feature input to the user state estimation model. Similarly the user state estimation model is an input for the predictive model.

The on-line learning mode involves the adjustment of user state estimation weights based on the incoming data sets, state classifications, and predictions. Predictions can be displayed on the data visualization software module.

Test Results of One Example Embodiment:

A model training study was conducted consistent with the user state estimation systems and methods disclosed. One objective for the study was to generate data sets that would allow a user state model of workload to be trained within the defined methods. For the scope of this example, the results focused primarily on model classification accuracy in relation to related published work. Secondary objectives of this study were to validate that subjective workload ratings to be used for training the workload model indeed correspond to the intended task difficulty, and conduct exploratory analysis on the degree to which workload fluctuations correspond to performance fluctuations.

The task environment for the study was based upon a modified version of the Air Force Multi-Attribute Task Battery (AF_MATB). This PC-based aviation simulation requires an operator to perform an unstable tracking task while simultaneously monitoring warning lights and dials, responding to simulation-generated auditory requests to adjust radio frequencies, and managing simulated fuel flow rates using various key presses. The rationale for using this task environment was threefold. First, MATB has been used as a testbed to train and develop other models of operator workload, which provides our approach with a benchmark for comparison. Second, MATB allows for linear titration of workload on a high-resolution scale, which provides the necessary task conditions to model beyond "low versus high workload" prior to injecting noise. Third, MATB has long and rich history of research findings that provide a deep understanding of how each task module affects operator workload, as well as the interactions between these factors.

Ten participants served as operators of the AF_MATB system for this study. The only requirement for participation was a familiarity with computer-based systems.

Task difficulty was the only independent variable (IV) for this study. This variable was selected because task difficulty manipulation has been an effective method for inducing varying levels of operator workload. To obtain the highest possible level of model granularity, 15 levels of task difficulty were used that intend to linearly span the full range of workload (i.e., low to high). Accordingly, this study employed a one-way experimental design in which a single IV (task difficulty) was manipulated across 15 conditions in order to assess its effects on each dependent variable (DV). All participants experienced the same 15 conditions; however, the sequence of conditions was counterbalanced to mitigate order effects.

The dependent variables (DVs) were physiological, self-reported, and performance measures collected from participants. Physiological measures included EEG, ECG, and eye-tracking activity (e.g., pupil diameter, fixations, blinks, etc.). Self-reported measures included antecedent lifestyle factors (e.g., demographics, level of exercise, video game experience), recent behavioral factors that can affect physiological state (e.g., sleep quality, current sleepiness, caffeine and food intake), and subjective workload assessments of each condition as measured via the NASA Task Load Index (TLX) scale. Performance measures included primary task performance on the AF_MATB tracking task (distance from centerpoint) and secondary task performance on the lights/gauges task (response time and accuracy).

Each participant went through two sessions: training and data collection. During the training session, participants acquired hands-on training by operating the system during practice scenarios ranging across easy, medium, and hard difficulty conditions. The goal was to eliminate learning effects during the data collection phase to the extent possible. For the data collection session, participants operated the AF_MATB environment through 15 five-minute scenarios while being monitored with physiological sensors and behavioral data capture software. Each of the 15 scenarios varied by task difficulty and was presented in a quasi-randomized order with five blocks of three scenarios per block. The three blocks in each scenario consisted of a low, medium, and high difficulty block. Physiological sensors collected data on eye movements, blinks, pupil diameter, EEG, and ECG. At the end of each trial, participants completed the NASA TLX questionnaire provided electronically on the AF_MATB.

Within the scope of this study, there were several ways to evaluate the utility of trained model results. First, the absolute error (expressed as mean absolute difference percent) between the model's output and the physiological noise-injected self-report value of workload upon which the model was trained were evaluated, which came to an average of 35% for all participants across all trials. For some participants, the average error across trials reached as low as 15%, although other participants produced greater than 50% error. The conclusion was that while many valuable inputs were collected that account for the majority of workload variance for specific individuals, there could be individual differences that were not sufficiently measured.

Second, the classification accuracy of the trained model when applied retroactively to participant data without providing the model with any direct workload-related input was analyzed. While categorization is not the ultimate goal of this approach, it is useful as a means for comparing this work to known benchmarks in the literature. Using classification accuracy for low versus high workload, the prototype model produced mean 82.7% accuracy when averaged for entire trials, and 75.7% accuracy on a per five-second basis. The study also went a step further to randomly removing two participants from the training set and applying the adjusted model to these removed participants. When averaged for entire trials, the adjusted model produced a mean 87.5% accuracy for low versus high classification for these two participants, and 77.8% on a per five-second basis. When considering our use of continuous high-resolution output as the basis of these classifications—as well as the small sample size and our inclusion of outliers—these results appear to compare favorably to similar work. In addition, our preliminary analysis on the benefits of on-line model training techniques (which are not reported here due to intended scope) has revealed promising trends with regard to additional accuracy generated due to dynamic model weight adjustments over time based on the individual performer.

While the per five-second classification accuracy of the state estimation model is difficult to empirically validate at this time (i.e., it is not feasible to obtain self-report data every five seconds for comparison), these results provide a quality baseline standard from which to expand work.

Secondary objectives of this study were to validate that subjective workload ratings to be used for training the workload model indeed correspond to the intended task difficulty, and conduct exploratory analysis on the degree to which workload fluctuations correspond to performance fluctuations. Correlation between participants' self-reported NASA TLX ratings and intended experimental difficulty (1-15) was approximately 0.67, demonstrating that workload was indeed reasonably well connected to the intended task difficulties of scenarios. This assumption was further validated by grouping continuous workload measures used for model training based on intended task difficulty/workload: Low (difficulties 1-5), Medium (difficulties 6-10), and High (difficulties 11-15). Based on these groupings, there was a statistically significant difference between mean continuous workload measures used for model training across each of three groups ($p<0.0001$). Furthermore, the study analyzed the addition of the noise injection algorithm to the NASA TLX responses to generate the continuous workload estimates for model training. When averaging the resulting continuous workload estimates across trials, we obtained a correlation of $r=0.99$ with the actual reported NASA TLX values, which demonstrated the noise injection algorithm did not overly skew workload responses.

Figure 6:
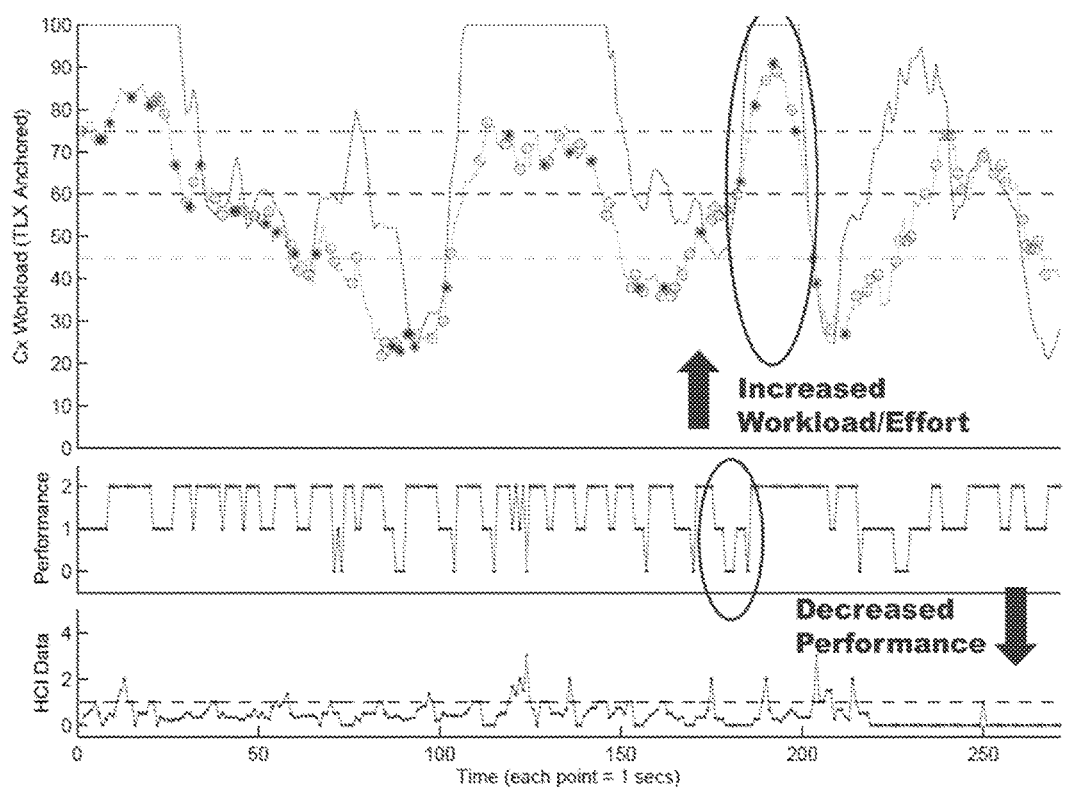
FIG. 6 illustrates the results of a user workload estimation enhanced to reflect an interval synchronized with performance and human-computer interaction (HCI) data inputs.

Lastly, at an exploratory level the study investigated the degree to which the model's estimates of workload provided identifiable clues to when performance decrements might occur. This was an informal analysis done to obtain a realistic expectation as to how frequently performance decrements could be identified proactively, using workload as the "leading indicator" and/or "trailing indicator" of their occurrence. The example illustration in FIG. 6 demonstrates one recurring trend in which a performance decrement can serve as a leading indicator of workload spikes, followed by subsequent behavioral changes in reaction to these effects.

This study tested an approach for establishing real-time estimates of user states on a continuous, high-resolution scale for the purpose of improving the ability to employ effective adaptive aiding strategies for performance augmentation.

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

We claim:

1. A computer based method to estimate a user state, the method comprising:
   receiving a plurality of first inputs at an intermittent interval;
   receiving a plurality of second inputs at a frequent interval;
   injecting a plurality of third inputs as a noise input into the plurality of first inputs at a non-random interval to create a plurality of enhanced first inputs whereby the plurality of enhanced first inputs correspond to the plurality of second inputs at the frequent interval;
   inputting the enhanced first inputs and the plurality of second inputs into a state estimation model whereby a user state can be estimated based on the plurality of second inputs; and
   estimating the user state based on the plurality of second inputs.

2. The computer based method of claim 1 wherein the noise input comprises a physiological correlate for the user state.

3. The computer based method of claim 2 wherein the noise input is injected into the plurality of first inputs according to an empirical relationship of the known physiological correlate to the first inputs.

4. The computer based method of claim 2 wherein the noise input is injected into the plurality of first inputs according to an empirical relationship of the physiological correlate to the first inputs.

5. The computer based method of claim 2 wherein the physiological correlate for the user state comprises a ratio of electroencephalogram (EEG) measures comprising a Frontal Midline Theta data over a Parietal Midline Alpha for the user state of a user workload.

6. The computer based method of claim 1 wherein the state estimation model comprises a relational database containing a weighted relationship of the plurality of second inputs to the plurality of first inputs.

7. The computer based method of claim 6 wherein the plurality of second inputs comprise a plurality of physiological inputs of a user and the plurality of first inputs comprise a plurality of state inputs of the user.

8. The computer based method of claim 1 further comprising inputting the enhanced first inputs and the plurality of second inputs into a machine learning model to create the state estimation model.

9. The computer based method of claim 8 wherein the machine learning model comprises an artificial neural network.

10. The computer based method of claim 9 wherein the artificial neural network is configured to find a mathematical relationship between a physiological feature and a state measurement.

11. The computer based method of claim 1 wherein the plurality of first inputs comprises a self-reported data of the user state.

12. The computer based method of claim 1 wherein the plurality of second inputs comprises at least one selected from a group comprising:
 a performance measure; and
 a situational measure.

13. The computer based method of claim 1 further comprising:
 receiving a plurality of enhanced actual first inputs and a plurality of actual second inputs;
 retraining the state estimation model with the plurality of enhance actual first inputs and the plurality of actual second inputs to create a retrained state estimation model; and
 estimating the user state based on the plurality of actual second inputs.

14. The computer based method of claim 13 wherein the retraining the state estimation model comprises inputting a plurality of enhanced actual first inputs and a plurality of actual second inputs into a machine learning model to create the retrained state estimation model.

15. The computer based method of claim 1 wherein:
 the estimate of the user state comprises an objective measure of a cognitive state of a trainee in a computer based training simulator; and
 the cognitive state comprises one selected from a group comprising:
  a real-time engagement of the trainee in a training situation, and
  a real-time workload of the trainee in the training situation.

16. The computer based method of claim 1 wherein the estimate of the user state comprises an objective measure of a cognitive state of a trainee in a computer based training simulator and the method further comprises:
 presenting a training situation to the trainee through a user interface; and
 adapting a interface based on objective measure of the cognitive state of the trainee.

17. A computer based method to estimate a state of a user, the method comprising:
 receiving a plurality of first inputs at an intermittent interval;
 receiving a plurality of second inputs at a frequent interval;
 injecting a noise input into the plurality of first inputs at the frequent interval to create a plurality of enhanced first inputs whereby the plurality of enhanced first inputs correspond to the plurality of second inputs at the frequent interval;
 inputting the enhanced first inputs and the plurality of second inputs into a state estimation model whereby a state of a user can be estimated based on the plurality of second inputs; and
 estimating a future state of the user at a future time utilizing the state estimation model.

18. The computer based method of claim 17 further comprising:
 modifying a user interface based on the future state of the user.

19. The method of claim 18 wherein the step of modifying the user interface based on the future state of the user comprises:
 eliminating an unnecessary information set from a user display; and
 displaying a necessary information set based on the future state of the user.

20. A computer based system for estimating a user state, the computer based system comprising:
 a processor;
 a non-transitory computer readable medium having a computer readable program code embodied therein, said computer readable program code configured to be executed to implement a method comprising:
  receiving a plurality of first inputs at an intermittent interval;
  receiving a plurality of second inputs at a frequent interval;
  injecting a plurality of third inputs as a noise input into the plurality of first inputs at a non-random interval to create a plurality of enhanced first inputs whereby the plurality of enhanced first inputs correspond to the plurality of second inputs at the frequent interval;
  inputting the enhanced first inputs and the plurality of second inputs into a state estimation model whereby a user state can be estimated based on the plurality of second inputs; and
  estimating the user state based on the plurality of second inputs.

* * * * *